United States Patent [19]

Newberry et al.

[11] 3,979,402
[45] Sept. 7, 1976

[54] THIAZOLE DERIVATIVES

[75] Inventors: Robert Anthony Newberry, Portsmouth; Brian John Bushell, Southampton, both of England

[73] Assignee: John Wyeth & Brother, Maidenhead, England

[22] Filed: Feb. 24, 1975

[21] Appl. No.: 552,097

[30] Foreign Application Priority Data

Feb. 27, 1974 United Kingdom............. 8870/74

[52] U.S. Cl............................. 260/302 R; 424/270
[51] Int. Cl.[2]................................. C07D 277/22
[58] Field of Search................. 260/302 R; 424/270

[56] References Cited
OTHER PUBLICATIONS

D. Jerassi et al., "J. of Organic Chem.," vol. XV, pp. 694–699 (1950).

*Primary Examiner*—Nicholas S. Rizzo
*Assistant Examiner*—D. B. Springer

[57] ABSTRACT

This invention relates to novel thiazole derivatives having the formula:

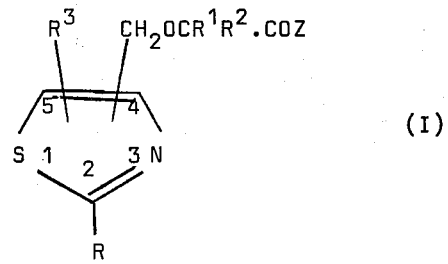

wherein R represents an unsubstituted or substituted aryl radical; $R^1$ and $R^2$ independently represent hydrogen or lower alkyl; $R^3$ represents hydrogen or lower alkyl; and —COZ represents an amide group; a carboxylic acid group or an ammonium or pharmaceutically acceptable alkali metal or alkaline earth metal salt thereof; or an ester group of formula —COOR[4] wherein $R^4$ represents an alkyl, aralkyl or aryl radical, which exhibit antilipemic activity.

5 Claims, No Drawings

THIAZOLE DERIVATIVES

This invention relates to novel thiazole derivatives, possessing pharmacological activity, to processes for preparing them, and to pharmaceutical compositions containing them.

In particular this invention provides novel thiazole derivatives having the formula:

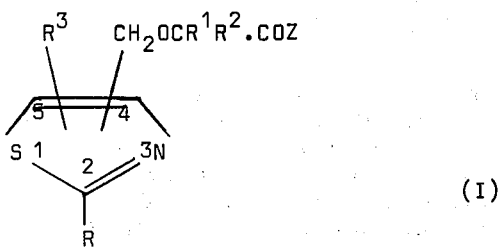

wherein R represents an unsubstituted or substituted aryl radical; $R^1$ and $R^2$ independently represent hydrogen or lower alkyl; $R^3$ represents hydrogen or lower alkyl; and —COZ represents an amide group; a carboxylic acid group or an ammonium or pharmaceutically acceptable alkali metal or alkaline earth metal salt thereof; or an ester group of formula —COOR$^4$ wherein $R^4$ represents an alkyl, aralkyl or aryl radical. Preferably $R^4$ when alkyl is lower alkyl and when aralkyl is aryl lower alkyl.

By the expression "lower" used in connection with alkyl is meant an alkyl group which contains from 1 to 6 carbon atoms and includes both straight and branched chains.

The term "alkali metal" includes alkali metals such as sodium, potassium, lithium and the like. The term alkaline earth metal includes magnesium, calcium and the like.

In the structure depicted by formula (I) the group $R^3$ may be in either of positions 4 or 5, the remaining position having the group —CH$_2$OCR$^1$R$^2$COZ. Preferably $R^3$ is in position 5.

Examples of R are phenyl or phenyl substituted by one or more groups which may be the same or different selected from halogen (for example fluorine, chlorine or bromine), lower alkyl (for example methyl, ethyl, propyl or butyl), lower alkoxy (for example methoxy, ethoxy, propoxy or butoxy), nitro, amino, alkylenedioxy (for example methylenedioxy) and trihaloalkyl (for example trifluoromethyl). Other groups represented by R include naphthyl (for example 2-naphthyl) which may be optionally substituted by one or more of the same groups as mentioned above for phenyl. Preferably R is phenyl or monohalophenyl, e.g. p-chlorophenyl.

Examples of $R^1$, $R^2$, $R^3$ and $R^4$ when they are representative of lower alkyl groups are methyl, ethyl, n-propyl, iso-propyl and n-butyl. Preferably $R^1$ and $R^2$ are both methyl. $R^3$ is preferably hydrogen. Examples of $R^4$ when aralkyl are benzyl and phenethyl groups. When $R^4$ is aryl it may be exemplified by phenyl. The group —COZ is preferably a carboxylic acid group or an ester of formula —COOR$^4$ wherein $R^4$ is lower alkyl.

The novel compounds of this invention possess pharmacological activity, in particular antilipemic activity. The antilipemic activity of a compound of this invention is established by two methods. Firstly, the compound being tested is orally administered to each member of a group of young male rats which had been fed a hypercholesterolemic diet for three weeks. The rats are grouped on the basis of their equal average serum cholesterol concentration determined on 0.01 milliliters of serum separated from tail blood collected in a capillary tube. The compound being tested is administered orally one or twice a day for these consecutive days. The serum cholesterol is determined on the fourth day and compared to the average of the group of untreated rats. Antilipemic activity is demonstrated by a lowering of the serum cholesterol. The potency of the test compound is expressed as the percent activity of concomitantly run tests employing clofibrate as the standard. The test procedure is repeated with normal chow-fed rats to determine the hypolipemic effect in the normal host.

Representative of the activity of the compounds of this invention is α-(2-p-chlorophenylthiazol-4-methyloxy)-α-methylpropionic acid which in the above test was found to be particularly active at a dose level of 50 mpk exhibiting 180% of the antilipemic activity of clofibrate. In the same test the corresponding ethyl ester was also particularly active at 50 mpk dose level exhibiting 170% the activity of clofibrate.

The second method of testing for antilipemic activity comprises subcutaneously administering the test compounds daily for nine days to adult male rats. On the tenth day a blood sample is taken and analysed for cholesterol. The results are expressed as the percent activity of concomitantly run tests employing estrone as standard.

Again in this test α-(2-p-chlorophenylthiazol-4-methyloxy)-α-methylpropionic acid and its corresponding ethyl ester had particularly good activity exhibiting 4,400% and 2,400% respectively the lipid depressant activity of estrone at 25 mpk dose levels.

The compounds of this invention may also exhibit other pharmacological activities, e.g. CNS depressant activity and/or inhibition of blood platelet aggregation. For the latter activity the following test procedure is used:

Compounds were tested for their capacity to inhibit adenosine diphosphate (ADP) induced reduction of circulating blood platelets in control and treated groups of male Sprague Dawley rats. A control cardiac blood sample is taken and the compound is given to the experimental group at a starting dose of 100 mg/kg or lower depending on the nature of the compound under test. After 30 minutes 15 mg/kg of ADP is injected into the leg vein. Cardiac blood samples are taken at 20, 40 and 60 seconds. The control group is given only ADP. Platelet counts are made on all blood samples with a Coulter Counter, the results plotted, and the percentage of inhibition determined. Active compounds are run at lower concentrations, and the results are expressed as the lowest dose showing significant inhibition of the ADP effect.

Compounds possessing the ability to inhibit blood platelet aggregation are of value in the treatment of vascular disease, particularly in the treatment or prevention of vascular thrombosis in mammals.

In the above test ethyl α-(2-phenylthiazol-4-methoxyloxy)-α-methylpropionate exhibited good activity at 50 mpk when administered orally.

The present invention also includes processes for preparing the novel compounds of formula (I). A first general method for preparing the compounds of formula (I) comprises reacting a thiazole of formula:

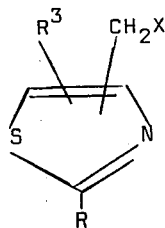

(II)

wherein R and R³ are as hereinbefore defined and X represents a halogen, with a compound of formula:

HO—CR¹R². COZ      III.

wherein R¹ and R² are as defined in connection with formula I and —COZ is an ester group of formula —COOR⁴ wherein R⁴ is as hereinbefore defined, and if desired converting the product to a corresponding compound of formula (I) wherein —COZ is an amide group, or a carboxylic acid group or an ammonium or pharmaceutically acceptable alkali metal or alkaline earth metal salt thereof. The reaction is preferably carried out in an inert solvent and in the presence of an alkali metal or alkali metal hydride, for example sodium hydride. Preferably X is chlorine or bromine.

A second method for preparing compounds of formula (I) comprises reacting a thiazole of formula:

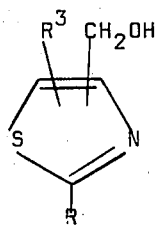

(IV)

wherein R and R³ are as hereinbefore defined, with a compound of formula:

X—CR¹R². COZ      V.

wherein R¹ and R² are as hereinbefore defined, X is halogen, and —COZ is as hereinbefore defined except an amide group; and, if desired, converting the product to a corresponding compound of formula (I) wherein —COZ is another group as defined in connection with formula (I).

The reaction is preferably carried out in an inert solvent and in the presence of an alkali metal, for example sodium, or an alkali metal hydride.

Yet another process for preparing the compounds of formula (I) having the structure depicted by the formula:

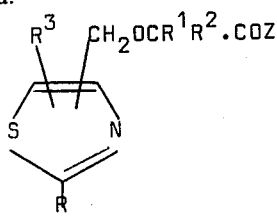

(Ia)

wherein R, R¹, R², R³ and —COZ are as defined in connection with formula (I) comprises reacting a compound of formula:

XCHR³—CO—CH₂-O-CR¹R². COZ      VI.

wherein R¹, R² and R³ are as hereinbefore defined, X is a halogen, for example chlorine, bromine or iodine and —COZ is an amide group or an ester group of formula —COOR⁴ wherein R⁴ is as hereinbefore defined; with a compound of formula:

R—CSNH₂      VII.

wherein R is as hereinbefore defined, and if desired converting the product formed to a corresponding compound of formula (I) wherein —COZ is another group as defined in connection with formula (I). This reaction may be carried out in a diluent or solvent, for example ethanol and it may be accelerated or completed by the application of heat.

Yet a further process for preparing compounds of formula (I) having the structure depicted by the formula:

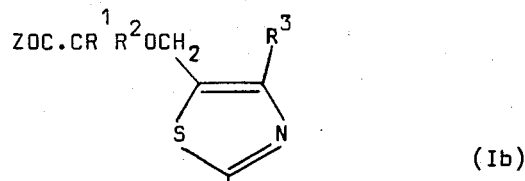

(Ib)

wherein R, R¹, R², R³ and —COZ are as defined in connection with formula (I); comprises reacting a compound of formula:

R³COCHX—CH₂OCR¹R²·COZ      VIII.

wherein R¹, R² and R³ are as defined above; X is halogen, for example chlorine, bromine or iodine; and —COZ is an amide group or an ester group of formula —COOR⁴ wherein R⁴ is as hereinbefore defined; with a compound of formula:

R—CSNH₂      VII.

wherein R is as hereinbefore defined, and if desired converting the product formed to a corresponding compound of formula (I) wherein —COZ is another group as defined above in connection with formula (I). This reaction may conveniently be carried out in a diluent or solvent, for example ethanol and it may be accelerated or completed by the application of heat.

It will be apparent to any one skilled in the art that once a compound of formula (I) having a particular —COZ group has been prepared then this compound may be converted to a corresponding compound of formula (I) wherein —COZ is one of the other groups as mentioned in connection with formula (I). For example, when —COZ is an ester function, this may be hydrolysed to the free acid or saponified to a pharmaceutically acceptable alkali metal or alkaline earth metal salt of the free acid. Alternatively, the ester may be converted to the amide by ammonolysis. When —COZ is a free carboxylic acid function this may be esterified to an ester function. The esters of formula I ($R^4$ is alkyl) may be prepared by standard methods, such as for example, by treating a solution of the free acids with diazomethane or other appropriate diazohydrocarbons, such as diazoethane, 1-diazo-2-ethylpentane, and the like. The alkali metal or alkaline earth metal carboxylates of the invention can also be prepared by mixing stoichiometrically equivalent amounts of the free acids of formula I, in aqueous solvent with alkali metal or alkaline earth metal bases, such as sodium, potassium, lithium, magnesium and calcium hydroxides or carbonates, and the like then freeze drying the mixture to leave the product as a residue. The ammonium salts can be prepared by mixing the free acids, with aqueous ammonium and freeze drying the mixture to leave the product as a residue.

A further feature of this invention is the provision of a pharmaceutical composition comprising a compound of formula (I) as hereinbefore defined in conjunction with one or more pharmaceutically acceptable carriers. The carrier for the compositions can be solid, liquid or mixed solid-liquid, and any suitable carrier known in the art can be used. The particular carrier chosen will depend on the actual compound, the desired method of administration and standard pharmaceutical practice. The compositions may be in the form of, for example, tablets, capsules or solutions.

The antilipemic agents of this invention may be administered orally or parenterally. The amount of the active compound needed to reduce the fat content of the blood to the desired level varies with the mode of administration to a certain extent as well as the condition of the individual under treatment with regard to age, fat concentration in the blood and depots, diet, transference factors of the gut and interstitial tissues and contributing factors such as the presence of hyperthyroidism, diabetes, cirrhosis of the liver or spleen, pancreatitis, et.

In practice, the compounds may be administered in unit doses containing from 25 to 500 milligrams of active ingredient, the remainder of the formulation constituting known adjuvants. The antilipemic compounds of the invention may be administered alone or in combination with pharmacologically acceptable carriers. For example, they may be administered orally in tablet or capsule form with conventional flavours, diluents, lubricants disintegrators or binding agents as may be required. They may be administered orally in the form of a solution or they may be injected parenterally. For parenteral administration they may be used in the form of a sterile solution containing other solutes, for example, enough saline or glucose to make the solution isotonic.

The present invention also provides a process of reducing the fat content of blood in a warm blooded animal which comprises administering to the said animal at least one compound of formula (I) as hereinbefore defined.

The following Examples illustrate the invention:

EXAMPLE 1

α-(2-p-Chlorophenylthiazol-4-methyloxy)-α-methylpropionic acid

Ethyl 2-hydroxyisobutyrate (16.25 gm, 0.123 moles) in 50 ml. of dimethyl formamide (DMF) was slowly added to a stirred suspension of 6.0 gm NaH (50% dispersion in oil, 0.125 moles) in 100 ml. of DMF. After stirring for 1 hour at 20°C a solution of 30 gm of 2-(p-chlorophenyl)-4-chloromethylthiazole (0.123 moles) in 150 ml. of DMF was slowly added and the mixture stirred at room temperature for 2 days. The mixture was then poured into 1 liter of water, extracted with benzene (3 × 250 ml.), washed with 200 ml. of water, dried with $MgSO_4$ and evaporated to give the ethyl ester of the title compound as an oil (38.0 gm).

This crude ester (38.0 gm) was refluxed overnight with 300 ml. of ethanol, 20 ml. of water and 15 gm of NaOH, and evaporated to give the sodium salt of the title compound as a solid. This was dissolved in 500 ml. of water, washed with ether (4 × 200 ml.), acidified with concentrated HCl, extracted into chloroform (2 × 250 ml.), washed with water (1 × 200 ml.), dried with $MgSO_4$ and evaporated to give the title compound as a solid (11.0 gm; m.p. 136°–8°C). This was recrystallised from aqueous ethanol (9.0 gm, m.p. 137°–8°C.).

Microanalysis: Found: C,53.8; H, 4.5; N, 4.7% $C_{14}H_{14}ClNO_3S$ requires:C, 53.9; H, 4.5; N, 4.5%

EXAMPLE 2

Ethyl α-(2-p-chlorophenylthiazol-4-methyloxy)-α-methylpropionate

The product from Example 1 (5.0 gm, 0.016 moles) was refluxed overnight in 100 ml. of absolute ethanol containing 5 ml. of concentrated $H_2SO_4$. The mixture was evaporated to give an oil which was taken up in 100 ml. of chloroform, washed with $Na_2CO_3$ solution and brine, dried with $MgSO_4$ and evaporated to give an oil (5.2 gm) which readily solidified. Recrystallisation from aqueous ethanol gave 3.3 gm of the title compound, m.p. 63°–4°C.

Microanalysis: Found C, 56.6; H, 5.4; N, 4.4% $C_{16}H_{18}ClNO_3S$ requires:C, 56.6; H, 5.3; N, 4.1%

EXAMPLE 3

α-(2-Phenylthiazol-4-methyloxy)-α-methylpropionic acid

Ethyl 2-hydroxyisobutyrate (19.5 gm, 0.148 moles) in 50 ml. DMF was slowly added over 30 minutes to a stirred suspension of NaH (50% dispersion in oil, 7.1 gm, 0.148 moles) in 100 ml. DMF. After stirring at room temperature for 1 hour, a solution 2-phenyl-4-chloromethylthiazole (31.0 gm, 0.148 moles) in 100 ml. DMF was added over 1 hour. The mixture was stirred for 1 day at 35°C, poured into 1 liter of water, extracted three times with 250 ml. of ether, washed with 250 ml. of water, dried with $MgSO_4$ and evaporated to dryness to give 33.3 gm of the crude ester of the title compound.

The crude ester (33 gm) in 200 ml. of ethanol was refluxed for 4 hours with 60 gm of NaOH and 100 ml. of water. The mixture was evaporated, diluted with 500 ml. of water and washed with two times 250 ml. of ether. it was then acidified with concentrated HCl, extracted into two times 250 ml. of ether, washed with 250 ml. of water and dried with $MgSO_4$. On evaporation an oil formed which readily solidified. Recrystallization from benzene/60–80 petrol gave the title compound as fawn crystals (12.4 gm, m.p. 78°–80°C.).

Microanalysis: Found: C,60.5; H, 5.4; N, 5.1% $C_{14}H_{15}NO_3S$ requires: C,60.8; H,5.5; N, 5.1%

EXAMPLE 4

Ethyl α-(2-phenylthiazol-4-methyloxy)-α-methylpropionate

A mixture of 6.0 gm of α-2-phenylthiazol-4-methyloxy)-α-methylpropionic acid (0.022 moles), 100 ml. of absolute ethanol and 1 ml. of concentrated $H_2SO_4$ were refluxed for 2½ hours, and evaporated to an oil. This oil was taken up in 200 ml. of chloroform, washed in turn with 100 ml. of water, two times 200 ml. of saturated $NaHCO_3$ solution and 100 ml. of water and dried with $MgSO_4$. On evaporation the title compound was obtained as a brown oil (5.7 gm).

Microanalysis: Found: C,62.9; H, 6.3; N,4.8% $C_{16}H_{19}NO_3S$ requires: C,62.9; H, 6.3; N,4.6%

EXAMPLE 5

α-(2-p-Bromophenylthiazol-4-methyloxy)-α-methylpropionic acid

Using a procedure analogous to Example 1, ethyl 2-hydroxyisobutyrate may be reacted with 2-(p-bromophenyl)-4-chloromethylthiazole to give the ethyl ester of the title compound. This may be hydrolysed in the manner of Example 1 to give the title compound.

EXAMPLE 6

α-(2-p-Fluorophenylthiazol-4-methyloxy)-α-methylpropionic acid

Using a procedure analogous to Example 1, ethyl 2-hydroxyisobutyrate may be reacted with 2-(p-fluorophenyl)-4-chloromethylthiazole to give the ethyl ester of the title compound. This may be hydrolysed in the manner of Example 1 to give the title compound.

EXAMPLE 7

α-(2-[3,4-Dichlorophenyl]thiazol-4-methyloxy-α-methylpropionic acid

Using a procedure analogous to Example 1, ethyl 2-hydroxyisobutyrate may be reacted with 2-(3,4-dichlorophenyl)-4-chloromethylthiazole to give the ethyl ester of the title compound. This may be hydrolysed in the manner of Example 1 to give the title compound.

EXAMPLE 8

α-(2-[2,5-Dimethylphenyl]thiazol-4-methyloxy)-α-methylpropionic acid

Using a procedure analogous to Example 1, ethyl 2-hydroxyisobutyrate may be reacted with 2-(2,5-dimethylphenyl)-4-chloromethylthiazole to give the ethyl ester of the title compound. This may be hydrolysed in the manner of Example 1 to give the title compound.

EXAMPLE 9

α-(2-p-Methoxyphenylthiazol-4-methyloxy)-α-methylpropionic acid

Using a procedure analogous to Example 1, ethyl 2-hydroxyisobutyrate may be reacted with 2-(p-methoxyphenyl)-4-chloromethylthiazole to give the ethyl ester of the title compound. This may be hydrolyzed in the manner of Example 1 to give the title compound.

EXAMPLE 10

α-(2-m-Trifluoromethylphenylthiazol-4-methyloxy)-propionic

Using a procedure analogous to Example 1, ethyl 2-hydroxypropionate may be reacted in 2-(m-trifluoromethylphenyl)-4-chloromethylthiazole to give the ethyl ester of the title compound. This may be hydrolysed in the manner of Example 1 to give the title compound

EXAMPLE 11

α-(2-p-Chlorophenylthiazol-4-methyl-5-methyloxy)-α-methylpropionic acid

Using a procedure analogous to Example 1 ethyl 2-hydroxyisobutyrate may be reacted wtih 2-(p-chlorophenyl)-4-methyl-5-chloromethylthiazole to give the ethyl ester of the title compound. This may be hydrolysed in the manner of Example 1 to give the title compound.

EXAMPLE 12

Benzyl α-(2-p-chlorophenylthiazol-4-methyloxy)-α-methyl propionate

Using a procedure analogous to Example 2, α-(2-p-chlorophenylthiazol(-4-methyloxy)-α-methylpropionic acid may be reacted with benzyl alcohol to give the title compound.

EXAMPLE 13

Phenyl α-(2-p-chlorophenylthiazol-4-methyloxy)-α-methylpropionate

Using a procedure analogous to Example 1 Phenyl 2-hydroxyisobutyrate may be reacted with 2-p-chlorophenyl-4-chloromethylthiazole to give the title compound.

EXAMPLE 14

α-(2-p-Chlorophenylthiazol-4-methyloxy)-α-methylpropionamide

Ethyl α-(2-p-chlorophenylthiazol-4-methyloxy-α-methylpropionate, prepared according to Example 2, may be reacted with ammonia under pressure to give the title compound.

We claim:
1. A compound having the formula:

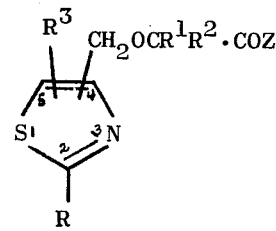

wherein R represents phenyl or phenyl mono-substituted by a halogen, lower alkyl, lower alkoxy, nitro, amino, methylene dioxy, or trifluoromethyl group; $R^1$ and $R^2$ independently represent hydrogen or lower alkyl; $R^3$ represents hydrogen or lower alkyl; and —COZ represents the amide group, the carboxylic acid group or the ammonium or a pharmaceutically acceptable alkali metal or alkaline earth metal salt thereof, or an ester group of formula —COOR⁴, wherein R⁴ represents a lower alkyl, phenyl lower alkyl, or phenyl radical; said lower alkyl, lower alkoxy, or phenyl lower alkyl groups having an alkyl chain of from 1 to 6 carbon atoms.

2. A compound as claimed in claim 1 which is α-(2-p-chlorophenylthiazol-4-methyloxy)-α-methyl-propionic acid or a pharmaceutically acceptable alkali metal salt thereof.

3. A compound as claimed in claim 1 which is Ethyl α-(2-p-chlorophenylthiazol-4-methyloxy)-α-methyl-propionate.

4. A compound as claimed in claim 1 which is α-(2-phenylthiazol-4-methyloxy)-α-methylpropionic acid or a pharmaceutically acceptable alkali metal salt thereof.

5. A compound as claimed in claim 1 which is Ethyl α-(2-phenylthiazol-4-methyloxy)-α-methylpropionate.

* * * * *